United States Patent
Kong et al.

(10) Patent No.: US 11,617,729 B2
(45) Date of Patent: Apr. 4, 2023

(54) USES OF GUANIDINE HYDROCHLORIDE AS A DRUG FOR TREATING CANCERS/TUMORS

(71) Applicants: Yanping Kong, Shijiazhuang (CN); Jinhong Liu, Shijiazhuang (CN)

(72) Inventors: Yanping Kong, Shijiazhuang (CN); Jinhong Liu, Shijiazhuang (CN)

( * ) Notice: Subject to any disclaimer, the term of this patent is extended or adjusted under 35 U.S.C. 154(b) by 151 days.

(21) Appl. No.: 16/925,260

(22) Filed: Jul. 9, 2020

(65) Prior Publication Data
US 2021/0154159 A1 May 27, 2021

(30) Foreign Application Priority Data
Nov. 22, 2019 (CN) .......................... 201911153206.7

(51) Int. Cl.
*A61K 31/155* (2006.01)
*A61P 35/00* (2006.01)

(52) U.S. Cl.
CPC ............ *A61K 31/155* (2013.01); *A61P 35/00* (2018.01)

(58) Field of Classification Search
CPC .............................. A61K 31/155; A61P 35/00
See application file for complete search history.

(56) References Cited

U.S. PATENT DOCUMENTS 7,927,612 B2 * 4/2011 Yu ........................ A61K 45/06
424/278.1

OTHER PUBLICATIONS

Cancerprevention, 2022, https://www.cancer.gov/about-cancer/causes-prevention#:~:text=Cancer%20prevention%20is%20action%20taken,can%20prevent%20cancer%20from%20developing.*

* cited by examiner

*Primary Examiner* — Sun Jae Yoo
(74) *Attorney, Agent, or Firm* — Novoclaims Patent Services LLC; Mei Lin Wong

(57) ABSTRACT

The uses of guanidine hydrochloride as a drug for treating cancers/tumors. Guanidine hydrochloride can destroy the formation of hydrogen bonds by polar molecules on the surface of cancer cells and the macromolecules taken up, thereby demonstrating that guanidine hydrochloride can inhibit the uptake by cancer cells. The present invention provides new uses of guanidine hydrochloride in the treatment of subjects suffering from cancers/tumors and prevention of recurrence after cancer operation. The dose of guanidine hydrochloride administration is 10-35 mg/kg a day. The hydrochloride dose of the guanidine has a significant inhibitory effect on the uptake of DNA by cancer cells, which in turn can effectively inhibit the proliferation of cancer cells; besides, the inhibition rate of liver cancer tumors 9 days after the injection of guanidine hydrochloride drugs can reach 42%, and the inhibition rate of lung cancer tumors 7 days after the injection of guanidine hydrochloride drugs reach 56.8%.

11 Claims, 5 Drawing Sheets

USES OF GUANIDINE HYDROCHLORIDE AS A DRUG FOR TREATING CANCERS/TUMORS

BACKGROUND OF THE PRESENT INVENTION

Field of Invention

The present invention belongs to the field of medicine, relates to the uses of guanidine hydrochloride in the treatment and prevention of cancers, in particular to the uses of guanidine hydrochloride as a drug for treating cancers/tumors.

Description of Related Arts

The alias of guanidine hydrochloride is carbamate hydrochloride, with the molecular formula $CH_5N_3 \cdot HCl$, the molecular weight of 95.54, and the structure of:

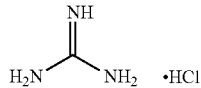

At present, guanidine hydrochloride is mainly used to treat muscle weakness caused by Eaton-Lambert syndrome (also called Eaton-Lambert myasthenic syndrome), since it increases the amount of acetylcholine released when nerves are excited, and also prolongs the depolarization and repolarization time of muscles.

There are many genetic mutations in cancer cells, which are mainly manifested by abnormal metabolism and rapid growth as well as the nutrient uptake process of cancer cells being significantly different from that of normal cells. Cancer cells with the function of pinocytosis (endocytosis) can take up glucose quickly and at a high level to meet the needs for their own rapid growth; and in the case of insufficient glucose, they can also directly use fatty acids and proteins in the blood to meet the needs for their own rapid growth. The derived pinocytosis (endocytosis) function of cancer cells is related to genetic mutations. For example, the function of liver cancer cells and breast cancer cells to take up macromolecular nucleic acids is also related to their pinocytosis function, while normal organ cells such as liver cells do not have this function. The rapid uptake of nutrients by cancer cells allows them to grow and proliferate quickly. When cancer cells take up macromolecules from the outside of the cells, these macromolecules (such as nucleic acids) first form non-covalent bonds such as hydrogen bonds with polar molecules on the surface of the cancer cells, and start pinocytosis to complete the uptake, thereby achieving cancer cell proliferation.

Therefore, fast-growing cancer cells need to quickly take up nutrients. If the uptake by cancer cells is inhibited, the growth of cancer cells will also be inhibited.

SUMMARY OF THE PRESENT INVENTION

The present invention finds that guanidine hydrochloride can destroy or interfere with the formation of hydrogen bonds by polar molecules on the surface of cancer cells and the macromolecules taken up, thereby inhibiting the rapid uptake by cancer cells. Experiments have shown that guanidine hydrochloride inhibits the growth of cancer cells. This finding has a profound impact on the uses of guanidine hydrochloride as a cancer cell growth inhibitor, and enables the present invention to identify new therapeutic applications, especially in the field of treatment of cancers.

Therefore, according to the present invention, the uses of guanidine hydrochloride as a drug for treating cancers/tumors are provided.

Wherein, patients to be treated are those suffering from cancers/tumors.

Patients to be prevented are those who have undergone cancer operation and need prevention of cancer recurrence.

Guanidine hydrochloride may be administered alone, and may be administered in any convenient drug form, such as tablets and liquid preparations, and through routes such as oral, intravenous and intervention, preferably administered orally. It may also be administered in combination with other drugs. In this indication, for an adult, guanidine hydrochloride is administrated at an initial dose of 125 mg, three times a day, the dose is increased every three days, and the dose is increased by 125-500 mg/time/day until the final dose is 10-35 mg/kg a day, or higher depending on the condition and constitution of the patient, or until the patient has side effects. If side effects occur, it is reduced to the previous dose.

According to the present invention, administration of guanidine hydrochloride to patients needing treatment can treat and prevent cancers/tumors. Tests have shown that the appropriate dose of guanidine hydrochloride (10-35 mg/kg a day) has a significant inhibitory effect on the uptake of DNA by cancer cells, which in turn can effectively inhibit the proliferation of cancer cells; besides, the inhibition rate of liver cancer tumors 9 days after the injection of guanidine hydrochloride drugs can reach 42%, and the inhibition rate of lung cancer tumors 7 days after the injection of guanidine hydrochloride drugs reach 56.8%. The experimental results show that guanidine hydrochloride significantly inhibits the cancer cells of animals suffering from a cancer/tumor and has obvious technical effects, so it can be clearly used for clinic purposes. Clinically, the above dosage of guanidine hydrochloride may be adjusted according to the condition of patients.

The present invention is applicable to cancer/tumor patients and patients to be prevented, wherein the patients to be prevented are those who have undergone cancer operation and need prevention of cancer recurrence.

DETAILED DESCRIPTION OF THE PREFERRED EMBODIMENT

Figure 1:
FIG. 1 is a fluorescent experiment image of the inhibition of DNA uptake by liver cancer cells after injection of 0 ng/mL triiodothyronine in Embodiment 1.
Figure 2:
FIG. 2 is a fluorescent experiment image of the inhibition of DNA uptake by liver cancer cells after injection of 1 ng/mL triiodothyronine in Embodiment 1.
Figure 3:
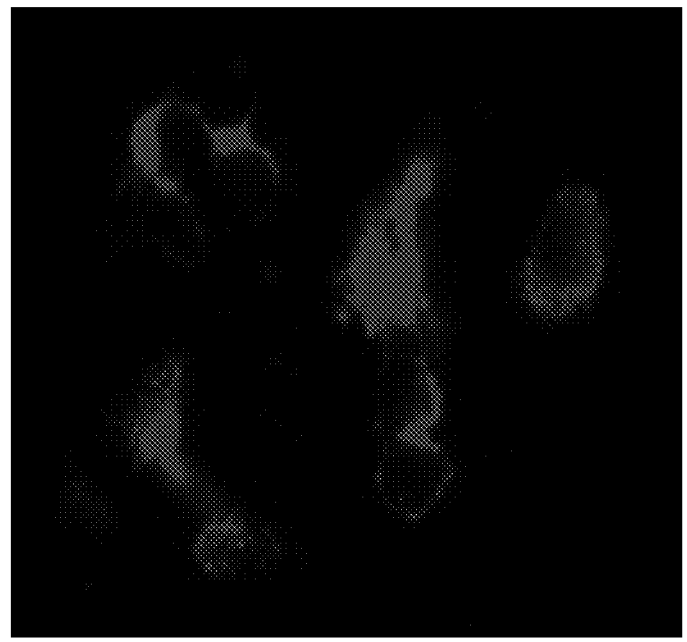
FIG. 3 is a fluorescent experiment image of the inhibition of DNA uptake by liver cancer cells after injection of 50 ng/mL triiodothyronine in Embodiment 1.
Figure 4:
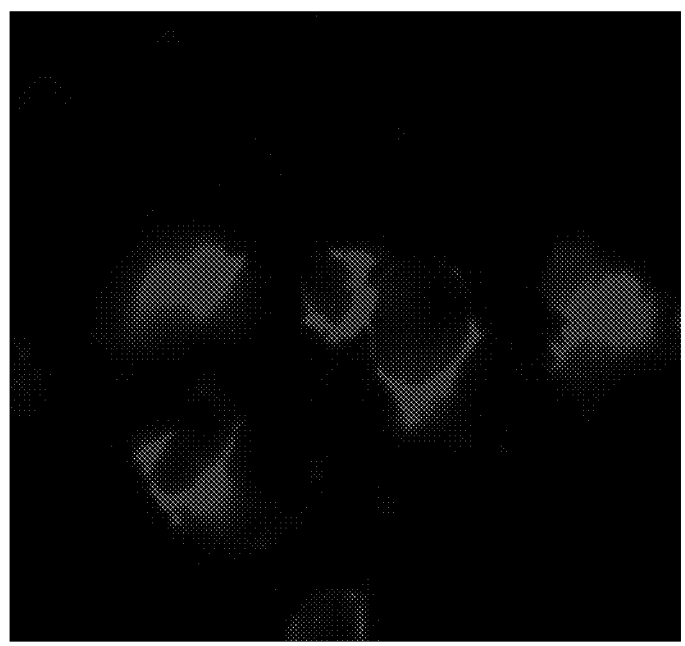
FIG. 4 is a fluorescent experiment image of the inhibition of DNA uptake by liver cancer cells after injection of 100 ng/mL triiodothyronine in Embodiment 1.
Figure 5:
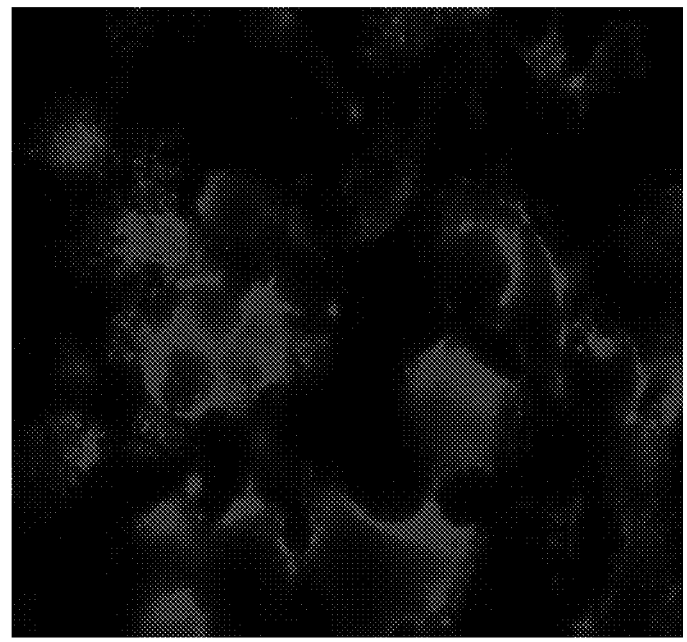
FIG. 5 is a fluorescent experiment image of the inhibition of DNA uptake by liver cancer cells after injection of 0 mmol/L guanidine hydrochloride in Embodiment 1.
Figure 6:
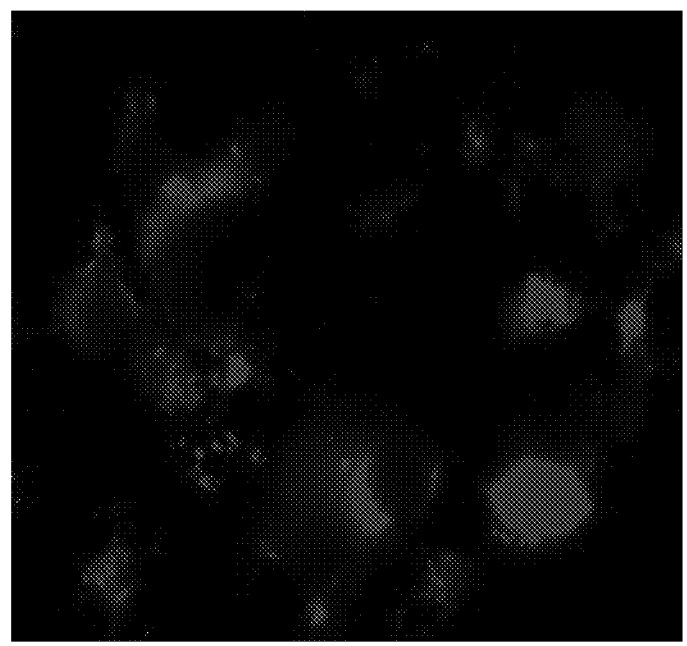
FIG. 6 is a fluorescent experiment image of the inhibition of DNA uptake by liver cancer cells after injection of 1 mmol/L guanidine hydrochloride in Embodiment 1.
Figure 7:
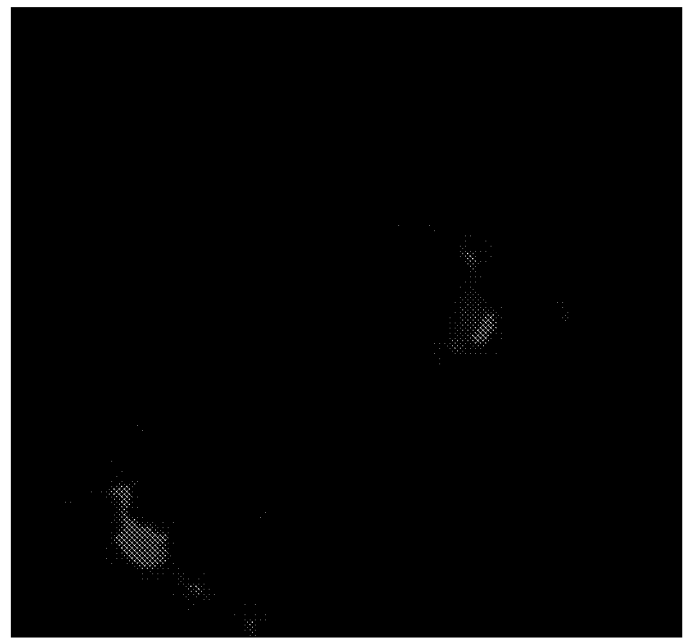
FIG. 7 is a fluorescent experiment image of the inhibition of DNA uptake by liver cancer cells after injection of 25 mmol/L guanidine hydrochloride in Embodiment 1.
Figure 8:
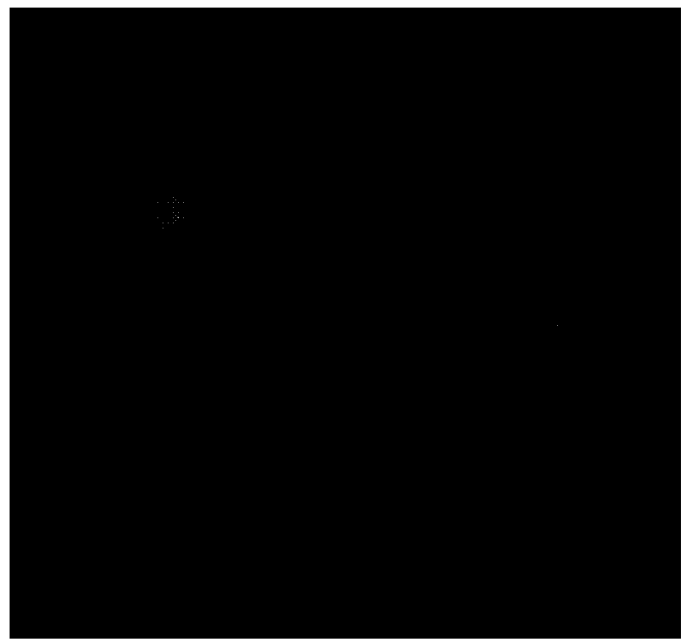
FIG. 8 is a fluorescent experiment image of the inhibition of DNA uptake by liver cancer cells after injection of 50 mmol/L guanidine hydrochloride in Embodiment 1.

The present invention will be further described in detail below through specific embodiments. It should be understood that the described embodiments are only used to explain the present invention and not to limit the present invention.

The fluorescent labeling kit (FISH) is purchased from the US company MIRUS, and operated according to the kit's instructions;

PCR polymerase and CellTiter 96® AQueous One Solution kit are purchased from the company Promega;

G-50 Sephadex (purification column) is purchased from the Life Science Department of GE (China) Healthcare Group;

Liver cells LO2 and liver cancer cells Huh7 come from the cell bank ATCC;

1640 medium, FBS (fetal bovine serum) and DMEM medium are purchased from Shanghai Jiake Biotechnology Co., Ltd.;

guanidine hydrochloride, PBS, formalin, phenol-chloroform, triiodothyronine (T3) and 96-well plates are purchased from Sigma-Aldrich;

The model of the fluorescence microscope is TCS SP, and purchased from the company Leica;

Both H22 mouse liver cancer cells and LLC lung cancer cell strains are provided by Hebei Medical University;

SPF grade Kunming mice and SPF grade CK57BL mice are purchased from Beijing Vital River Laboratory Animal Technology Co., Ltd.

Embodiment 1 Guanidine Hydrochloride Test on the Inhibition of DNA Uptake by Liver Cancer Cells 1.8 KB of AFP (alpha feto protein) DNA is obtained through PCR (polymerase chain reaction), extracted with phenol-chloroform and adjusted to a concentration of 1 µg/mL. 5 µg of DNA is taken, and Rhodamine (fluorescent marker) is added. The mixture is allowed to stand at 37° C. for 1 hour, and purified in a G-50 Sephadex (purification column).

1640 medium is taken, and FBS (fetal bovine serum) is added, wherein the mass of FBS (fetal bovine serum) is 10% of that of 1640 medium. Put the mixture aside.

Eight groups of liver cancer cells Huh7 are inoculated into a 1640 medium respectively containing 10% FBS (fetal bovine serum) and cultured at 37° C. for 12 hours in an incubator containing 5% $CO_2$.

The four groups of them are added with 0 mmol/L, 1 mmol/L, 25 mmol/L and 50 mmol/L guanidine hydrochloride, further cultured in the above incubator for 24 hours, added with fluorescently labeled DNA, and then cultured for another 8 hours. Cells obtained through culture are rinsed 3 times with PBS and fixed with 4% formalin. The cells fixed as described above are photographed with a fluorescence microscope. Likewise, the same procedure is carried out to prepare control groups, but guanidine hydrochloride is replaced with triiodothyronine (T3). The concentration of T3 is: 0 ng/mL, 1 ng/mL, 50 ng/mL and 100 ng/mL respectively.

See FIG. 1-4 for the inhibition of fluorescently labeled DNA uptake by liver cancer cells after injection of triiodothyronine. See FIG. 5-8 for the inhibition of fluorescently labeled DNA uptake by liver cancer cells after injection of guanidine hydrochloride. As can be seen from the figures that in FIG. 5-8, the content of labeled DNA in the cells significantly decreases with the increase of the concentration of guanidine hydrochloride, indicating that guanidine hydrochloride can significantly inhibit the uptake of DNA, and there is a dose-effect relationship; however, the control groups in FIG. 1-4 do not affect the uptake.

Figure 9:
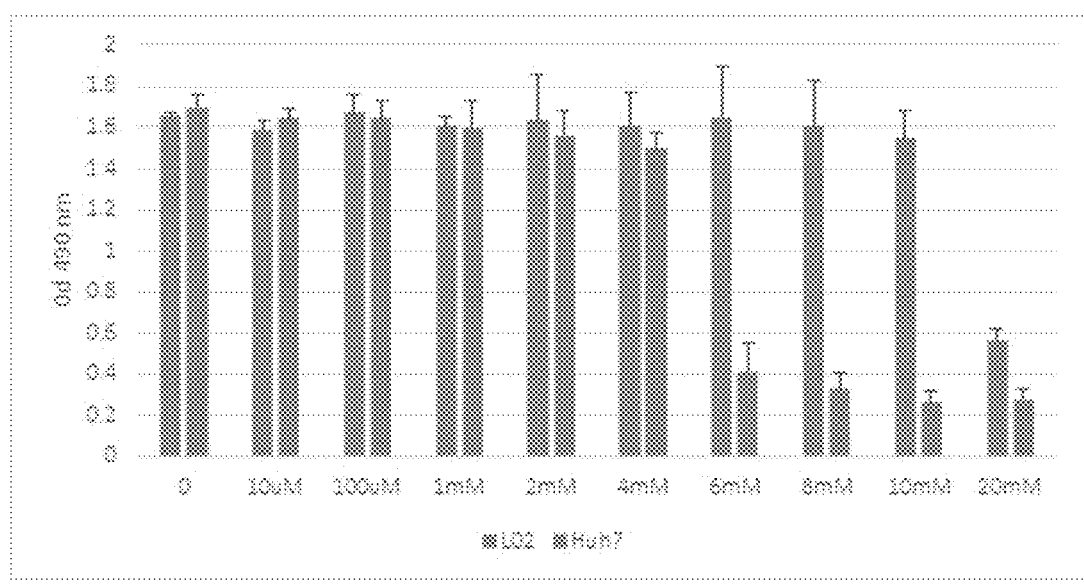
FIG. 9 is a diagram of the inhibition of liver cancer cell proliferation by guanidine hydrochloride in Embodiment 2.

Embodiment 2 Guanidine Hydrochloride Test on the Inhibition of Liver Cancer Cell Proliferation Liver cells LO2 and liver cancer cells Huh7 are inoculated into a 1640 medium containing 10% FBS (fetal bovine serum) respectively, and cultured at 37° C. for 12 hours in an incubator containing 5% $CO_2$. Liver cells LO2 and liver cancer cells Huh7 obtained as described above are taken and inoculated into a 96-well plate respectively, with each well containing $6\times10^3$ cells, and cultured at 37° C. for 12 hours in an incubator containing 5% $CO_2$. guanidine hydrochloride of different contents is added to the 96-well plates until the final concentration of guanidine hydrochloride in each well of the 96-well plates is: 0 µmol/L, 10 µmol/L, 100 µmol/L, 1 mmol/L, 2 mmol/L, 4 mmol/L, 6 mmol/L, 8 mmol/L, 10 mmol/L and 20 mmol/L respectively, and the plates are cultured for 72 hours to quantify cell proliferation. The CellTiter 96® AQueous One Solution kit is used to determine the cells. 20 µL of analytical reagents are added and readings are taken at 490 nm absorbance. As can be seen from the diagram of the inhibition of liver cancer cell proliferation by guanidine hydrochloride in FIG. 9, when guanidine hydrochloride reaches 6 mmol/L, it begins to significantly inhibit the growth of cancer cells Huh7 but does not affect the growth of liver cells LO2; when the concentration of guanidine hydrochloride increases to 20 mmol/L, both liver cells LO2 and liver cancer cells Huh7 are significantly inhibited.

Embodiment 3 Guanidine Hydrochloride Test on the Inhibition of the Growth of Mouse Liver Cancer Tumors Preparation of tumor cell suspension: H22 mouse liver cancer cells are inoculated into a 1640 medium containing 10% FBS (fetal bovine serum), and cultured at 37° C. for 12 h in an incubator containing 5% $CO_2$. When the cells grow to the logarithmic phase, the above medium is prepared into a cell suspension, and the concentration of H22 mouse liver cancer cells is controlled to $1\times10^6$ cells/mL to obtain the tumor cell suspension for later use.

Building of animal tumor model: 30 SPF grade Kunming mice, male and (20±2) g, are taken. The above mice are kept in a laboratory without particular pathogens and randomly divided into 3 groups, namely normal saline group, low-dose guanidine hydrochloride group, and high-dose guanidine hydrochloride group, 10 mice in each group. The right armpit skin of mice in each group is disinfected with alcohol, and 0.2 mL of the above tumor cell suspension is drawn with a 1 mL syringe, and inoculated into the disinfected part of the mice by slow hypodermic injection. All mice are given sufficient water and feed, the litter is kept dry and the tumor growth of the mice is observed. Generally, 7 days after modeling, obvious tumor nodules can be felt under the armpits of the mice, which means that the modeling was successful.

Control test: for the above-mentioned animal tumor model, the low-dose guanidine hydrochloride group is injected intraperitoneally at a 240 mg/kg dose twice a day (0.3 mL/time) for 9 consecutive days; the high-dose guanidine hydrochloride group is injected intraperitoneally at a 480 mg/kg dose twice a day (0.3 mL/time) for 9 consecutive days; the normal saline group is given normal saline twice a day (0.3 mL/time) for 9 consecutive days; and the tumor volume is monitored, where the tumor volume $(cm^3) = \frac{1}{2}$ length×width$^2$.

The tumor inhibition rate is separately calculated by the formula: the tumor inhibition rate=(average volume of mouse tumors in the normal saline group−average volume of mouse tumors in the guanidine hydrochloride groups)/average volume of mouse tumors in the normal saline group× 100%. The specific tumor inhibition is shown in Table 1:

TABLE 1

List of the Inhibition of the Growth of Mouse
Liver Cancer Tumors by Guanidine Hydrochloride

|  | Third day | Sixth day | Ninth day | Inhibition rate (ninth day) |
|---|---|---|---|---|
| Normal saline | 0.55 | 2.24 | 4.11 | — |
| Low-dose guanidine hydrochloride group | 0.55 | 2.16 | 3.11 | 24% |
| High-dose guanidine hydrochloride group | 0.54 | 1.47 | 2.37 | 42% |

As can be seen from Table 1, the tumor inhibition rate of the low-dose guanidine hydrochloride group 9 days after the injection of drugs is 24%, and the tumor inhibition rate of the high-dose guanidine hydrochloride group 9 days after the injection of drugs is 42%. Therefore, guanidine hydrochloride can significantly inhibit the growth of liver cancer tumors.

Embodiment 4 Guanidine Hydrochloride Test on the Inhibition of the Growth of Mouse Lung Cancer Tumors Preparation of tumor cell suspension: LLC lung cancer cell strains are inoculated into a DMEM medium containing 10% FBS (fetal bovine serum), and cultured at 37° C. for 12 h in an incubator containing 5% $CO_2$. When the cells grow to the logarithmic phase, the above medium is prepared into a cell suspension, and the concentration is $1\times10^6$ cells/mL to obtain the lung cancer cell suspension for later use.

Building of animal tumor model: 20 SPF grade CK57BL mice, male and (20±2) g, are taken. The above mice are kept in a laboratory without particular pathogens. The right armpit skin of the mice is disinfected with alcohol, and 0.2 mL of the above tumor cell suspension is drawn with a 1 mL syringe, and inoculated into the disinfected part of the mice by slow hypodermic injection. All mice are given sufficient water and feed, the litter is kept dry and the tumor growth of the mice is observed. Generally, about 10 days after modeling, obvious tumor nodules can be felt under the armpits of the mice, which means that the modeling was successful.

Control test: The above mice are randomly divided into 2 groups, namely normal saline group and guanidine hydrochloride group, 10 mice in each group. The normal saline group is given normal saline once a day (0.3 mL/time) for 7 consecutive days; the guanidine hydrochloride group is injected intraperitoneally at a 480 mg/kg dose once a day (0.3 mL/time) for 7 consecutive days; and the tumor volume is monitored on the first day, the third day, the fifth day and the seventh day, where the tumor volume $(cm^3) = \frac{1}{2}$ length×width$^2$.

The tumor inhibition rate is separately calculated by the formula: the tumor inhibition rate=(average volume of mouse tumors in the normal saline group−average volume of mouse tumors in the guanidine hydrochloride groups)/average volume of mouse tumors in the normal saline group× 100%. The specific tumor inhibition is shown in Table 2:

TABLE 2

List of the Inhibition of the Growth of Mouse
Lung Cancer Tumors by Guanidine Hydrochloride

|  | First day | Third day | Fifth day | Seventh day | Inhibition rate on the seventh day |
|---|---|---|---|---|---|
| Saline | 0.5 | 1.18 | 2.08 | 4.19 | |
| Guanidine hydrochloride 480 mg/kg | 0.43 | 0.92 | 1.24 | 1.8 | 56.8% |

As can be seen from Table 2, the tumor inhibition rate of the guanidine hydrochloride group 7 days after the injection of drugs is 56.8%. Therefore, guanidine hydrochloride can significantly inhibit the growth of lung cancer tumors.

What is claimed is:

1. A method for treating cancers/tumors by administering guanidine hydrochloride alone as a single active ingredient.

2. The method according to claim 1, wherein the guanidine hydrochloride is administered to a patient suffering from a cancer/tumor.

3. The method according to claim 1, wherein the guanidine hydrochloride is administered to a patient having undergone a cancer operation to prevent a growth of cancer cells.

4. The method according to claim 1, wherein the guanidine hydrochloride interferes or destroys hydrogen bonds between polar molecules and ingested macromolecules on a surface of cancer cells and inhibits uptake by the cancer cells to the extent of inhibiting the growth of cancer cells.

5. The method according to claim 1, wherein a dose of the guanidine hydrochloride is 10-35 mg/kg a day.

6. The method according to claim 1, wherein a dose of the guanidine hydrochloride is gradually increased from 125 mg/time for three times a day to 10-35 mg/kg a day.

7. The method according to claim 1, wherein the guanidine hydrochloride is in the form of tablet or liquid preparation.

8. The method according to claim 4, wherein the guanidine hydrochloride is administered orally.

9. The method according to claim 4, wherein the guanidine hydrochloride is the single active ingredient which inhibits growth of cancer cells by inhibiting uptake of the cancer cells, and the guanidine hydrochloride is in the form of tablet or liquid preparation for oral administration.

10. The method according to claim 9, wherein an effective dose of the guanidine hydrochloride is 10-35 mg/kg a day.

11. The method according to claim 9, wherein a dose of the guanidine hydrochloride is gradually increased from 125 mg/time for three times a day to 10-35 mg/kg a day.

* * * * *